United States Patent [19]

Lillehoj

[11] Patent Number: 5,449,610
[45] Date of Patent: Sep. 12, 1995

[54] MONOCLONAL ANTIBODIES AGAINST CHICKEN T-LYMPHOCYTES

[75] Inventor: Hyun S. Lillehoj, W. Friendship, Md.

[73] Assignee: The United States of America, as represented by the Secretary of Agriculture, Washington, D.C.

[21] Appl. No.: 876,819

[22] Filed: Apr. 29, 1992

Related U.S. Application Data

[63] Continuation of Ser. No. 251,427, Sep. 29, 1988, abandoned.

[51] Int. Cl.$^6$ .................. C07K 3/00; C17Q 1/00; C17N 15/00; A01K 35/14
[52] U.S. Cl. .................. 435/7.24; 435/70.21; 435/172.2; 435/240.27; 530/388.75
[58] Field of Search .................. 530/387, 388.75; 435/7.24, 70.21, 172.2, 240.27

[56] References Cited

PUBLICATIONS

Hyun S. Lillihoj, "Production and Flow Cytometric Analysis of Monoclonal Antibodies Reactive with Subpopulations of Chicken Lymphocytes," In Avian Immunology, pp. 87-97, Alan R. Liss, Inc. (1987).

Marion M. Chan et al., "Identification of the Avian Homologues of Mammalian CD4 and CD8 Antigens," J. Immunol. 140: 2133-2138 (1988).

Elizabeth Houssaint et al., "Tissue Distribution and Ontogenic Appearance of a Chicken T Lymphocyte Differentiation Marker," Eur. J. Immunol. 15: 305-308 (1985).

K. Hala et al., "3. A Monoclonal Antibody Reacting with a Membrane Determinant Associated with T Cell Activation in the Chicken," J. Immunobiol. 168: 2 (1985) (Abstract).

Chen-lo H. Chen et al., "Chicken Thymocyte-Specific Antigen Identified by Monoclonal Antibodies: Ontogeny, Tissue Distribution, and Biochemical Characterization," Eur. J. Immunol. 14: 385-391 (1984).

J. Richard Pink et al. "Monoclonal Antibodies Against Chicken Lymphocyte Surface Antigens," Hybridoma 2: 287-296 (1983).

Vernon T. Oi et al., "Immunoglobulin-Producing Hybrid Cell Lines," In Selected Methods in Cellular Immunlogy, B. B. Mishell and S. M. Shiigi (eds.), pp. 351-372 (1980).

Primary Examiner—C. Warren Ivy
Assistant Examiner—Raymond Covington
Attorney, Agent, or Firm—M. Howard Silverstein; Curtis P. Ribando; John D. Fado

[57] ABSTRACT

Seven murine hybridoma cell lines capable of secreting monoclonal antibodies that can identify subpopulations of chicken lymphocytes have been developed. Precursor cytotoxic and suppressor T lymphocytes, precursor helper lymphocytes, and mature T lymphocytes may be distinguished by use of these antibodies.

4 Claims, No Drawings

MONOCLONAL ANTIBODIES AGAINST CHICKEN T-LYMPHOCYTES

This application is a continuation of application Ser. No. 07/251,427, filed Sep. 29, 1988 now abandoned.

BACKGROUND OF THE INVENTION

1. Field of the Invention

This invention relates to new hybridomas and monoclonal antibodies therefrom which recognize distinct antigens on subpopulations of chicken T-lymphocytes.

2. Abbreviations

Abbreviations or definitions used in the disclosure are as follows: BSA—bovine serum albumin; C—rabbit complement; ConA—concanavalin A; CTL—cytotoxic T lymphocytes; CTLA—chicken T lymphocyte antigen; DTT—dithiothreitol; EDTA—ethylene diamine tetraacetic acid; ELISA—lymphocyte binding enzyme linked immunosorbent assay; E:T—effector to target; FCM—flow cytometric; FCS—fetal calf serum; HBSS—Hanks balanced salt solution; IEL—intraepithelial lymphocytes; LGL—large granular lymphocytes; MAbs—monoclonal antibodies; MDV—Marek's disease virus; MHC—major histocompatibility complex; NK—natural killer; PBL—peripheral blood lymphocytes; PBS—phosphate buffered saline; PEG—polyethylene glycol; REV—reticuloendotheliosis virus; SD—standard deviation; SR—% spontaneous release; TR—total release.

3. Summary of Prior Art

The immune system of chickens has received much attention as a model for studying lymphocyte differentiation and human immunodeficiency states [Blaese et al., In Avian Immunology, A. A. Benedict (ed.), Plenum Publishing Co., New York, p. 155 (1977); Palladino et al., J. Immunol. 116:1673 (1976)]. However, although modern hybridoma technology has made it possible to separate mouse and human lymphocytes into functional subsets [Cantor and Boyse, J. Exp. Med. 141:1376–1389 (1975); Engleman et al., Proc. Natl. Acad. Sci. USA 78:1791–1795 (1981)], monoclonal antibodies defining subsets of chicken lymphocytes have not been generally available. Until recently, surface antigens distinguishing chicken thymus- and bursa-derived lymphocytes were detected using heteroantisera [Wick et al., Clin. Exp. Immunol. 15:237–249 (1973)]. The limitations of both allo- and xenoantisera can now be resolved by the generation of MAbs with the somatic cell hybridization techniques introduced by Kohler and Milstein [Nature 256:495 (1975)].

In mammals, a series of MAbs detecting surface antigens has enhanced our knowledge of functionally distinct subpopulations of lymphocytes [Kung et al., Science 206:347 (1979); Reinherz et al., J. Immunol. 123:2894 (1979); Reinherz et al., Proc. Natl. Acad. Sci. USA 77:1588 (1980); Ledbetter et al., J. Exp. Med. 153:319 (1981); Dialynas et al., J. Immunol. 131:2445 (1983)]. In chickens, subpopulations of chicken T lymphocytes with distinct helper [Grebenau et al., Eur. J. Immunol. 9:477 (1979); Sarvas et al., Scand. J. Immunol. 3:455 (1974); Chi et al., Eur. J. Immunol. 10:23 (1980)], suppressor [Chi et al., supra; Grebenau et al., supra; Lerman et al., Cell Immunol. 51:109 (1980)], or cytotoxic [Palladino et al., Dev. Compar. Immunol. 4:309 (1980); Chi et al., Cell Immunol. 64:246 (1981); Maccubin and Schierman, J. Immunol. 136:12 (1986)] activities have been described. Although cell surface antigens detecting subpopulations of chicken T lymphocytes have been detected by xenoantisera or alloantisera, only in a few cases have the relevant antigens been biochemically or functionally characterized [Peault et al. Eur. J. Immunol. 12:1047 (1982); Pink and Rijnbeek, Hybridoma 2:287 (1983); Houssaint et al., Eur. J. Immunol. 15:385 (1985)]. Some antigenic markers associated with subpopulations of avian T lymphocytes have recently been described [Chan et al., J. Immunol. 140:2133 (1988)], and analogies were drawn between the human and chicken lymphocyte antigens.

Four systems of T cell differentiation alloantigens have been reported in the chickens. They are Th-1 [Gilmour et al., Immunogenetics 3:549–563 (1976)], Ly-4 [Fredrickson et al., Immunogenetics 5:535–552 (1977)], CA1 and TA [Galton and Ivanyi, Eur. J. Immunol. 7:241–246, 457–459 (1977)]. These antigens were detected using polyclonal antisera absorbed against bursa lymphocytes [Gilmour et al., supra]. Only a few monoclonal antibodies recognizing antigens on chicken T cells are available [Chen et al., Eur. J. Immunol. 14:385 (1984); Hala et al., Immunobiology 168:2 (1985); Houssaint et al., supra; Lillehoj, In Avian Immunology, Weber and Ewert (eds.), pp. 87–97, Alan R. Liss, Inc., New York (1987)], and most of these antibodies detect antigens expressed primarily on thymocytes. Two monoclonal antibodies that identify cell-surface antigens expressed on functionally distinct T-cell subpopulations in birds have been reported [Chan et al., supra]. Monoclonal antibodies detecting surface alloantigens of chicken lymphocytes will overcome the problems associated with the use of polyspecific antisera, such as the presence of antiviral antibodies and autoantibodies, difficulty in reproducing antisera and obtaining large amounts, and need to absorb sera to obtain required specificity.

The monoclonal antibodies described in this invention will allow the poultry industry and scientists working with poultry to isolate and investigate important subpopulations of lymphocytes for assessing immune status of the flock during infections or following vaccination. Since these monoclonal antibodies identify defined antigens or lymphocytes, the investigation of the role of these antigens in economically important diseases of poultry will now be possible.

SUMMARY OF THE INVENTION

It is an object of this invention to produce monoclonal antibodies useful to identify subpopulations of chicken lymphocytes and to assess the immune status of the flock.

Another object of the invention is to develop and propagate fused hybrid cell lines (hybridomas) which continuously produce monoclonal antibodies to chicken lymphocytes.

Additional objects of the invention will be set forth in the description which follows, and will become apparent to those skilled in the art upon examination of the specification or by practice of the invention.

DESCRIPTION OF THE PREFERRED EMBODIMENTS

Monoclonal antibodies of this invention were produced by techniques similar to those described by Lillehoj [supra].

Mice were immunized with chicken thymus or spleen cells, and a booster immunization of thymus lymphocytes was given a few weeks later. A few days after the final immunization, myeloma and immune spleen cells were fused in the presence of polyethylene glycol according to the procedure of Oi and Herzenberg [In Selected Methods in Cellular Immunology, Mishell and Shiigi (eds.), pp. 351–371, W. H. Freeman and Co., San Francisco (1980)].

Several days after fusion, supernatants from cultures containing hybridomas were tested by a lymphocyte binding enzyme linked immunosorbent assay. Hybridomas secreting lymphocyte binding antibodies were identified by sequential incubation with rabbit anti-mouse antisera, and hybridomas secreting antibodies of interest were cloned. Antibodies may be recovered in the supernatant of hybridoma cells grown in vitro or produced from ascites fluids produced by injecting mice with hybridoma cells.

Hybridoma cell lines of this invention designated CTLA1, CTLA3, CTLA4, CTLA5, CTLA6, CTLA8, and CTLA9 are continuously maintained by the United States Department of Agriculture in a laboratory located at: PDL, BARC-E, Bldg. 1040, USDA-ARS, Beltsville, Md. 20705.

Hybridoma cell lines CTLA 1 and CTLA 3 were deposited on Nov. 11, 1994, under the conditions of the Budapest Treaty with the American Type Culture Collection, Rockville, Md., and have been assigned numbers ATCC HB 11749 and ATCC HB 11750, respectively.

FCM Analysis of Cells Binding CTLA MAbs

Seven stable hybridomas secreting antibodies specifically binding to chicken T lymphocytes were established from several successful fusions of P3X63-Ag653 myeloma cells with murine splenic lymphocytes immunized with chicken thymus or splenic lymphocytes. These hybridomas were cloned by limiting dilution and their chicken T lymphocyte antigen (CTLA) binding MAbs were produced in ascites fluids. The isotypes and the tissue binding characteristics determined by FCM analysis of these 7 MAbs and anti-chicken Ia MAb are shown in Table I. Their reactivity pattern with T lymphocyte containing tissues from 2-week-old chickens allowed them to be subdivided into 3 groups. MAbs CTLA5 and 8 (group I) showed a similar staining pattern by reacting approximately 73% of thymus, 44% of spleen, and 51% of PBL, respectively. MAbs comprising group II (CTLA 3, 4, and 9) showed reduced binding, when compared to group I, of antigen on 43% of thymus, 36% of spleen, and 18% of PBL. Compared to groups I and II, MAbs of group III (CTLA 1 and 6) showed intermediate reactivity with thymus cells (58%) and reduced reactivity with spleen cells (13%). Their average 19% binding to PBL was similar to that of group II MAb. The T lymphocyte specificity of these MAbs is reinforced by the fact that none of them reacted with bursa (B lymphocyte enriched) cells from chickens 2 weeks of age. However, the bursa reactivity of group I MAbs was age dependent in that MAbs CTLA 5 and 8, which reacted with only 5–8% of cells from 2-week-old chickens, stained 31–52% bursal cells by 2 months (Table I). The antigens recognized by CTLA MAbs represent monomorphic determinants of chicken lymphocyte antigens, since both SC, FP, and other strains of chickens tested showed similar staining pattern.

TABLE I

Isotypes and Flow Cytometric Analysis of CTLA Monoclonal Antibodies

| Group | MAb | MAb[a] Isotype | Percent of cells positive (Mean + SD)[b] | | | |
|---|---|---|---|---|---|---|
| | | | Bursa | Thymus | Spleen | PBL |
| I | CTLA 5 | IG$_1$ | 8 ± 2(3)[c] | 74 ± 10(12) | 47 ± 10(6) | 56 ± 14(5) |
| | CTLA 8 | IG$_1$ | 5 ± 3(6)[d] | 72 ± 8(17) | 42 ± 8(9) | 47 ± 10(7) |
| II | CTLA 3 | IG$_1$ | 8 ± 4(7) | 50 ± 14(19) | 39 ± 18(13) | 23 ± 9(9) |
| | CTLA 4 | IG$_1$ | 8 ± 3(9) | 40 ± 23(23) | 36 ± 12(12) | 16 ± 7(10) |
| | CTLA 9 | IG$_1$ | 7 ± 4(9) | 40 ± 22(23) | 32 ± 13(14) | 15 ± 4(10) |
| III | CTLA 1 | IG$_2$ | 6 ± 3(7) | 56 ± 20(20) | 10 ± 6(16) | 17 ± 8(10) |
| | CTLA 6 | IG$_1$ | 8 ± 3(9) | 59 ± 26(15) | 16 ± 11(13) | 22 ± 8(7) |

[a]Isotypes were determined by Ouchterlony double immunodiffusion method using antisera specific for each isotype of mouse immunoglobulin (Miles).
[b]Numbers in the parentheses indicate number of FCM analyses performed on independent cell populations obtained from SC and FP chickens.
[c]31 ± 20(3) in 3-month-old chickens.
[d]52 ± 1(2) in 3-month-old chickens.

Long-term LGL cultures or established T and B cell lines were analyzed to further investigate the staining characteristics of the CTLA MAbs (Table II). In general, large granular lymphocytes (LGL) grown in IL-2 containing medium [Schat et al., Avian Pathol. 15:539–556 (1986)] stained brightly with MAbs CTLA 5 and 6. Two of three Marek's Disease virus (MDV) transformed cell lines were strongly stained with group III MAb CTLA 6. The staining patterns with group I MAb CTLA 5 varied from cell line to cell line as shown by faint staining of CU36 cells. None of the CTLA MAbs stained LSCC-RP9, a B cell line transformed by avian leukosis virus.

Effect of CTLA MAbs on Mitogen Inducted T-cell Proliferation

Splenic T lymphocytes were depleted by pretreatment with various MAb and rabbit C, and the remaining viable lymphocytes were stimulated with ConA for 3 days to investigate the effects of CTLA MAbs on T lymphocyte activation induced by ConA. The results shown in Table III demonstrate that pretreatment of spleen cells with MAbs CTLA 5 or 8 (group I) reduced ConA induced proliferation. Similarly, pretreatment of splenic T lymphocytes with MAbs CTLA 4 or 9 (group II) inhibited the ConA induced proliferative responses in a manner comparable to that produced by pretreatment with a mouse anti-Ia MAb. In contrast, pretreatment of spleen T cells with MAbs CTLA 1 or 6 (group III) resulted in substantially less inhibition compared to that seen with other groups.

Effect of CTLA MAbs on MHC-restricted Cytotoxicity

A previous study showed that splenic effector cells from REV-infected P-2a donor chickens did not lyse allogenic REV-infected target cells, whereas highly significant levels of lysis occur when syngenic REV-infected target cells were used [Weinstock and Schat, In Avian Immunology, Weber and Ewert (eds.), p. 253, Alan R. Liss Inc., New York (1987)]. Two different approaches were used to investigate the effects of CTLA MAbs on such MHC-restricted CTL activity. In the

TABLE II

MAb Staining of LGL and Marek's Disease Virus Transformed Cell Lines[a]

| Hybridoma MAb | LGL[b] | | Cell Lines[c] | | | |
|---|---|---|---|---|---|---|
| | A | B | CU41 | CU15 | CU36 | RP9 |
| CTLA 5 | 93[d] | 100[d] | 0 | 67 | 9 | 0 |
| CTLA 3 | 19[e] | 0 | 0 | 0 | 0 | 0 |
| CTLA 9 | 7[f] | 0 | 0 | 0 | 0 | 0 |
| CTLA 4 | 5 | 0 | 0 | 0 | 0 | 0 |
| CTLA 6 | 77[d] | 98[d] | 0 | 98 | 100 | 0 |

[a]Expressed as percentage of cells stained per samples. Approximately 44–100 cells were examined.
[b]Large granular lymphocytes (LGL) grown in the presence of IL-2 containing ConA conditioned medium for 28 days as described [Schat et al., Avian Pathol. 15: 539–556 (1986)].
[c]MDV-transformed T cell lines: MDCC-CU41 (P-2a chicken, RB-1B strain of MDV), CU15 (P2 chicken, GA-5 strain of MDV), CU36 (UCD-003 chicken, GA-5 strain of MDV), and LSCC-RP9m avian leukosis transformed B cell line.
[d]Majority strongly positive.
[e]2/59 strongly positive; 9/59 weakly positive.
[f]3/71 strongly positive.

TABLE III

Effect of MAb + Rabbit C Pretreatment on Mitogen Induced T Cell Proliferation[a]

| Hybridoma MAb | ($^3$H) – TdR Uptake ($\Delta$CPM) | Inhibition[b] |
|---|---|---|
| None | 63,828 | — |
| CTLA 5 | 3,192 | 95 ± 5 |
| CTLA 8 | 1,915 | 97 ± 7 |
| CTLA 4 | 7,660 | 88 ± 10 |
| CTLA 9 | 6,383 | 90 ± 21 |
| CTLA 1 | 42,127 | 34 ± 7 |
| CTLA 6 | 37,659 | 41 ± 5 |

[a]Elimination of lymphocytes binding each MAb was carried out first by incubating splenic or PBL lymphocytes with a MAb for 30 min at 4° C. Cells were then washed and incubated with rabbit anti-mouse serum. After 30 min incubation at 4° C., cells were washed three times and incubated for 45 min with complement (C) at 41° C. Mitogen stimulation was performed by incubating splenic T cells with RPMI 1640 medium alone (negative control) or Con A (5 μg/ml) for 3 days and blastogenesis determined by uptake of $^3$H-TdR.
[b]Percent inhibition was calculated by the following formula:
($\Delta$CPMCon A + MAb/$\Delta$CPMCon A + p3X) where $\Delta$CPM = CPM$_{Con\ A}$ − CPM$_{medium}$.

first group of experiments, splenic T lymphocytes obtained from REV-infected P-2a chickens were pretreated with different MAbs and rabbit C. The remaining lymphocytes were used as effectors in the CTL assay. Pretreatment of spleen cells with MAbs CTLA 5 (group I), 3, 4, or 9 (group II), but not MAb CTLA 6 (group III) in the presence of C resulted in significant reduction in the CTL activity compared to pretreatment with a mouse anti-rotavirus serum (positive control). Spleen cells pretreated with a mouse anti-chicken Ia MAb also reduced the CTL activity significantly. In second group experiments, CTLA MAbs were added to the CTL assay consisting of a coculture between P-2a (B17B17) effector spleen cells obtained from REV-infected chickens and REV-transformed P-2a target spleen cells. MAbs CTLA 3, 4, or 9 (group II) significantly inhibited this CTL activity. The choice of antibodies used in the blocking assay was based on the results of the depletion assay.

Effect of CTLA MAbs on NK Cell Activity

To test the effects of CTLA MAbs on non-MHC restricted cytotoxicity mediated by NK cells, MAbs CTLA 3, 4, 6, or 9 were added to an NK cell assay at the initiation of the assay. MAbs CTLA 3, 4, or 9 (group II) significantly inhibited NK cell activity ($P<0.05$), whereas MAb CTLA 6 (group III) did not interfere with NK cell activity. Addition of mouse anti-chicken Ia MAb did not reduce NK cell activity. These results were corroborated by pretreating effector cells with CTLA MAbs plus C and using the remaining cells in the NK assay. Again, MAbs CTLA 3, 4, or 9, but not anti-chicken Ia MAb, significantly inhibited NK activity ($P<0.05$). Furthermore, pretreatment of splenic effector cells obtained from P-2a chickens infected with SB-1 with MAb CTLA 3 significantly reduced NK cell activity against LSCC RP-9. Since an earlier study showed that cells mediating nonspecific cytotoxicity are present in chicken IEL (Chai and Lillehoj. Immunology 63:111 (1988)], the expression of these antigens and their distribution in the intestine were analyzed. Splenic T lymphocytes stimulated with ConA for 2 days or duodenum IEL obtained from normal chickens were stained with the CTLA MAbs 3 (group II) or 6 (group III). CTLA 3 MAb stained a substantially higher fraction of normal IEL and splenic ConA blast cells compared to P3X myeloma culture supernatant (negative control) or CTLA 6 MAb.

Molecular Weight Determinations of T Lymphocyte Antigens Recognized by CTLA MAbs The molecular weights of the surface antigens recognized by CTLA MAbs were determined by immunoprecipitation and polyacrylamide gel electrophoresis of $^{125}$I surface labeled detergent extracts of chicken thymus cells. MAbs CTLA 5 and 8 (group I) both immunoprecipitated two major bands of 65,000 and 45,000 daltons under reducing conditions. MAbs CTLA 1 and 6 (group III) both specifically immunoprecipitated one major band with an apparent molecular weight of 65,000 daltons under reducing conditions. Immunoprecipitation of $^{35}$S-labeled thymocyte extract with MAbs CTLA 1 and 6 showed 55,000 molecular weight band, presumably representing unmodified internal protein. MAbs CTLA 3 and 4 (group II) both immunoprecipitated a 33,000–35,000 dalton protein. In addition, MAb CTLA 3 also immunoprecipitated a large molecular weight 66,000 dalton protein.

This invention reports the generation of seven MAbs identifying chicken T lymphocyte antigens. Based upon the tissue distribution, associations with T lymphocyte activities and biochemical parameters of the CTLA identified by these MAbs, they were divided into three groups, as summarized in Table IV.

Comparison of these characteristics with those of mammalian T lymphocyte antigens suggest that the antigens recognized by MAbs CTLA 5 and 8 (group I) are analogous to the mammalian CD5 antigen, those recognized by MAbs CTLA 3, 4, and 9 (group II) are analogous to CD8, and those recognized by MAbs 1 and 6 (group III) are analogous to CD4.

TABLE IV
Summary of CTLA MAbs

| Group | Hybridoma MAb | Cell Specificity | M.W. | Mammalian Homolog |
|---|---|---|---|---|
| I | CTLA 5 & 8 | All mature T lymphocytes | 65,000 45,000 | CD5 |
| II | CTLA 3, 4, & 9 | Cytotoxic T lymphocytes Natural killer cells | 31–35,000 (66,000) | CD8 |
| III | CTLA 1 & 6 | Helper T lymphocytes | 65,000 | CD4 |

Furthermore, this invention provides new information concerning the functional and biochemical characteristics of avian "CD" antigens: (1) CD8 antigens are expressed on cells mediating MHC as well as non-MHC restricted cytotoxicity; (2) the avian CD8+ thymocyte subpopulation expressed a 65,000 dalton molecular species in addition to the lower molecular species of 33,000–35,000 daltons; and (3) adult bursa contain substantial proportion of cells expressing T cell markers.

FCM analysis indicated that group I MAbs, CTLA 5 and 8, identify antigens present on approximately 72–74% of thymus cells, 42–47% of spleen cells, and 47–56% of PBL. No significant reaction with bursa cells was observed in chickens younger than 3 weeks old. Pretreatment of spleen cells with MAbs CTLA 5 or 8 with C removed all the cells responsible for ConA or PWM induced proliferation and enriched for cells responding to lipopolysaccharide. Pretreatment of spleen cells with these MAbs reduced also the ability of these cells to mediate CTL or NK activity. However, when present during culture conditions, MAbs CTLA 5 and 8 were ineffective in blocking CTL or NK reactivity. Both MAbs immunoprecipitated 45 and 65 KDa proteins from $^{125}$I-labeled thymus extracts under reducing conditions. Taken together, these results suggest that MAbs CTLA 5 and 8 identify antigens present on mature T lymphocytes analogous to the mammalian CD5 antigen. The molecules detected by MAb CTLA 5 and 8 are similar in size to the 45–55 KDa and 65–70 KDa proteins detected by a rabbit anti-chicken T lymphocyte serum [Pink et al., Eur. J. Immunol. 11:517 (1981)]. Therefore, these two MAbs are unique among the MAbs thus far described that bind to avian T lymphocyte antigens in their similarity to CD5.

In mammalian species, CD5 antigens are expressed on all mature T cells and on some B cells [Beya and Miyasaka, Immunology 58:71 (1986); Hayakawa et al., J. Exp. Med. 157:202 (1983); Miyasaka et al., In Immunology of the Sheep, Morris and Miyasaka (eds.), p. 68, Editiones Roche, Basel (1985)]. The murine CD5 glycoprotein (Lyt-1) predominantly consisted of a single polypeptide chain of 67,000 daltons that showed extensive charge heterogeneity by two-dimensional gel electrophoresis as well as two or three lower molecular weight derivatives, depending on the lymphoid organ or T cell line from which the molecules were derived [Ledbetter et al., J. Exp. Med. 152:280 (1980)]. The human CD5+ (Leu-1+, Leu-2−) T lymphocyte subpopulation expressed a distinctive molecular species of 55,000 daltons [Reinherz et al., supra (1979)]. In guinea pigs MAb 8BE6, recognizing the human CD5 homologue, reacted with 80% of lymph node cells, 45% of spleen cells, and 10% of thymocytes [Chiba et al., J. Immunological Methods 63:247 (1983)]. It immunoprecipitated a predominant polypeptide of 68,000 daltons and a second polypeptide of 57,000 daltons, which may have represented a degradation product or nonglycosylated form of the larger species. In sheep, MAb ST-1a/b identified a 60–65 KDa and 67 KDa noncovalently linked glycoprotein dimer, the apparent analogue of the human CD5 molecule [Miyasaka et al., supra; Beya and Miyasaka, supra; Beya et al., Immunology 57:115 (1986)]. It was identified on all thymocytes and T cells but not B cells. Thus the antigens detected by MAbs CTLA 5 or 8 appear to be pan-T lymphocyte cell marker and the avian homologues of the mammalian CD5 antigens. Although both the human and mouse CD5 antigen are known to be expressed by a small subset of normal and leukemic B lymphocytes [Wang et al., J. Exp. Med. 151:1539 (1980); Hayakawa et al., supra], there was no indication that a significant population of B cells from 2-week-old chickens express the antigens defined by MAb CTLA 5 or 8. In this respect, the avian CD5 antigen is similar to that of sheep. However, I did observe a significant proportion of cells from the bursa of Fabricius that stained positive with these MAbs from 3-month-old chickens. These may have represented T cells that are known to be present in diffusely infiltrated areas (DIA) of the bursa of Fabricius described by Odend hal and Breazile [Am. J. Vet. Res. 41:255 (1980)]. They have previously shown that this DIA is a T cell-dependent area strategically located to ensure intimate contact with environmental antigens.

Tissue distributions of the antigens recognized by MAbs CTLA 3, 4, and 9 (group II) are similar to those of the antigens binding to CT8 MAb [Chan et al., supra]. Pretreatment of spleen cells with MAbs CTLA 4 or 9 resulted in a substantial reduction in the T lymphocyte response to ConA. They also blocked the anti-REV specific CTL activity. The antigens recognized by MAbs CTLA 3, 4, and 9 thus appear to be T lymphocyte surface antigens involved in MHC restricted cytotoxicity. In contrast, an anti-chicken Ia MAb did not block CTL activity. These results suggest that the antigens recognized by MAbs CTLA 3, 4, and 9, but not Ia antigens, are important in chicken MHC-restricted CTL function.

The receptors involved in nonspecific, MHC-unrestricted effector-target cell interactions and lysis continue to raise controversy [Hercend et al., Nature 301:158 (1983); Hercend et al., J. Exp. Med. 158:1547 (1983); Hersey and Bolhuis, Immunol. Today 8:233 (1987)]. MAbs CTLA 3, 4, and 9 blocked nonspecific cytotoxicity of cultured tumor cells mediated by NK cells, suggesting that the antigens recognized by these MAbs are on NK cells. NK cells, however, appear to express CD8 antigens at much lower density compared to CTL cells, since depletion with group III MAbs did not effectively remove NK cells. In contrast, MAb to chicken Ia antigens did not block NK cell mediated cytotoxicity. In mammals, several receptors including CD8 have been implicated in both MHC-restricted as well as MHC-unrestricted cytotoxicity [Hersey and Bolhuis, supra]. My results indicate that the CD8 antigens are also expressed on chicken cells involved in MHC-unrestricted cytotoxicity.

Recently, the presence of lymphocytes expressing the gamma and delta polypeptide chains of the T cell receptor (TCR1) were shown to be present in the intestinal mucosa of chickens [Bucy et al., FASEB J. 2:A446 (1988)]. The function of these TCR1-bearing cells has been suggested to involve immunesurveillance of epithelia. In this respect these cells are similar to mammalian dendritic epithelial lymphocytes present in the epidermis [Bergstresser et al., J. Invest. Derm. 81:286 (1983); Romani et al., J. Exp. Med. 161:1368 (1985); Koning et al., Science 236:834 (1987)]. TCR1 expressing cytotoxic cell lines have been isolated and shown to account for some non-MHC-restricted cytotoxic cells [Lanier and Phillips, Immunol. Today 7:132 (1986)]. Chicken intestinal IEL, like mammalian IEL, has a high percentage of cells that can mediate NK activity [Chai and Lillehoj, supra]. My results indicate that, like in humans, a large fraction of these cells express low levels of the CD8 antigen. This suggests that TCR1+, CD8+ IEL cells may mediate immunesurveillance in the intestinal epithelium of chickens and monitor the integrity of the cell layer that separates the internal from the external milieu.

MAbs CTLA 3 and 4 immunoprecipitated 33–35 KDa proteins from radioiodinated thymus cell extracts. MAb CTLA 3 also reacted with a 66 KDa species. The smaller protein precipitated by both MAbs is very similar in size to the molecule immunoprecipitated from $^{125}$I-labeled chicken PBL extracts by MAb CT8 [Chan et al., supra]. The larger MW band that I observed in the MAb CTLA 3 precipitates may represent an undissociated complex. In mice, the CD8 molecule immunoprecipitated from thymocyte extracts had subunits of 30, 34, and 38 KDa in SDS-polyacrylamide gels under reducing conditions [Ledbetter et al., supra (1981)]. The 66 KDa protein may represent an undissociated homodimer of the 33 KDa protein or a heterodimer of the 33 KDa species with an unidentified moiety.

Group III MAbs CTLA 1 and 6 stained approximately 56–59% of thymus cells, 10–16% of spleen cells, and 17–22% of PBL. Biochemical analysis of the antigens detected by MAbs CTLA 1 and 6 identified a 65 KDa protein. Furthermore, CTLA 6 MAb did not block NK or CTL responses, and pretreatment of spleen cells did not reduce cells mediating MHC or non-MHC restricted cytotoxicity. These molecules are functionally similar to human [Stewart et al., J. Immunol. 136:3773 (1986)], rat [Clark et al., Proc. Natl. Acad. Sci. USA 82:1649 (1987)], and mouse [Goding et al., Nature 317:425 (1985)] CD4 molecules. However, the apparent molecular weights of the antigens recognized by these MAbs are larger than that reported for CD4 molecules from mammalian species. Interestingly, most of MDV transformed T lymphocyte lines were positive for group III, CD4 specific MAb CTLA 2, and negative for group II, CD8 specific, MAbs CTLA 3, 4, and 9.

These results have revealed that the functional and biochemical analogies between human, mouse, and chicken T lymphocyte antigens are quite striking. The apparent conservation of the molecular structure and tissue distributions of these T lymphocyte "CD" antigens suggests that these surface molecules are not simply convenient markers for various T cell subpopulations with different functional capabilities. Rather, the maintenance of these structures during evolution may have occurred because they perform essential functions for the cells on which they are found. The availability of large numbers of MAbs for specific T cell subsets will allow for more feasible comparative studies and will enhance our basic knowledge of avian immunity.

The following examples are provided by way of illustration to explain the best mode of practicing the invention in greater detail. These examples are not to be construed as limiting the invention, which is defined by the claims.

EXAMPLE 1

Experimental Animals and Cell Lines

Embyronated eggs of inbred SC and FP chickens were obtained from Hy-Line International Production Center, Dallas Center, Iowa. P-2a ($B^{19}B^{19}$) chickens were hatched and maintained at the Department of Avian and Aquatic Animal Medicine, Cornell University. Development and characterization of these chickens were previously described [Weinstock and Schat, supra]. BALB/C mice were obtained from Charles River, Wilmington, Mass. Oubred nude mice were obtained from the National Institutes of Health, Bethesda, Md. The nonsecretor hybridoma cell lines, P3X63-Ag.653 (American Type Culture Collection, Rockville, Md.) and Fox-NY (Hiclone Lab, Logan, Utah) were used for cell fusions.

EXAMPLE 2

Preparation of Chicken Lymphocytes

Single cell suspensions of spleen, bursa, or thymus lymphocytes were prepared from freshly removed tissues. The tissues were minced and passed through a stainless steel No. 66 sieve (Thomas Scientific, Philadelphia, Pa.). PBL were prepared by Ficoll/Hypaque separation according to the manufacturer's specification (Pharmacia Fine Chemicals, Piscataway, N.J.). Intraepithelial lymphocytes (IEL) were prepared as described [Chai and Lillehoj, supra]. Briefly, duodenal c-loops, cut into 1–2 cm fragments, were washed in cold Hanks' balanced salt solution (HBSS) mediium, incubated in 10 mM dithiothreitol (DTT, Sigma, St. Louis, Mo.) in HBSS for 5 to 10 min at room temperature, gently stirred at 41° C. in 0.1 mM EDTA for 20 min, and rinsed with calcium- and magnesium-free HBSS. These supernatants were pooled, the cells isolated by centrifugation, washed twice, and resuspended in HBSS supplemented with 10% heat inactivated fetal calf serum (FCS). All single cell suspensions were passed quickly through nylon wool to remove dead cells.

EXAMPLE 3

Immunization and Fusion

Female BALB/c mice (6–8 weeks old) were immunized intravenously with $2\times10^7$ chicken thymus or spleen cells. An intravenous boost of thymus lymphocytes ($2\times10^7$) was given 5 weeks later. Three or four days later, myeloma and immune spleen cells were fused in the presence of 50% polyethylene glycol (PEG) 4000 in RPMI 1640 medium according to the procedure of Oi and Herzenberg [supra].

EXAMPLE 4

Screening and Cloning of Hybridomas

Seven or 10 days after fusion, supernatants from cultures containing hybridomas were tested by a lymphocyte binding enzyme linked immunosorbent assay (ELISA). Chicken lymphocytes ($1 \times 10^5$) were centrifuged in poly-L-lysine-treated wells of Nunc immunoassay plates (Thomas Scientific, Philadelphia, Pa.), and crosslinked with 0.05% cold glutaraldehyde in phosphate buffered saline (PBS) for 15 min. Crosslinking was stopped by the addition of 100 μM glycine in PBS supplemented with 0.1% bovine serum albumin (BSA) for 30 min. ELISA plates were pretreated for 5 min with 30% $H_2O_2$ followed by 10% BSA for 30 min. Supernatants from hybridomas were added and incubated for 2 hr at room temperature. Hybridomas secreting lymphocyte binding antibodies were identified by sequential incubations with rabbit anti-mouse or rabbit anti-rat serum (Miles Scientific, Naperville, Ill.), biotin-labeled goat anti-rabbit serum (Sigma, St. Louis, Mo.), streptavidin labeled peroxidase (Sigma), and orthonitrophenyldiamine (Sigma). The reaction was stopped with 0.5% citric acid, and the optical densities at 450 nm were determined using a Titertek Multiskan (Flow Laboratories Inc., McLean, Va.). Hybridomas secreting antibodies reactive with chicken lymphocytes of interest were cloned by limiting dilution in the presence of mouse thymus feeder cells. Ascites fluids were produced by injecting $1 \times 10^6$ hybridoma cells into BALB/c or nude mice that had been injected intraperitoneally with 2, 6, 10, 14-tetramethylpentadecane (Sigma).

The procedures for cloning by limiting dilution and antibody production are described by Oi and Herzenberg ["Immunoglobulin-Producing Hybrid Cell Lines," In Selected Methods in Cellular Immunology, Mishell & Shiigi (eds.), pp. 366–368, W. H. Freeman and Co. San Francisco (1980)], which is herein incorporated by reference.

EXAMPLE 5

Flow Cytometric (FCM) Analysis

FCM medium used to prepare samples was Hanks balanced salt solution (HBSS) without phenol red, supplemented with 3% heat inactivated FCS and 0.% $NaN_3$. Lymphocytes ($1 \times 10^6$) were incubated with 100 μl of appropriately diluted MAbs for 30 min on ice, followed with fluorescein conjugated affinity purified rabbit anti-mouse or rabbit anti-rat serum (Miles) for 30 min on ice. The cells were washed and subsequently analyzed on the EPICS V Dual Bench Flow Cytometer (Coulter Corporation, Hialeah, Fla.). The fluorescent signal was collected as the log of integrated fluorescence gated on forward angle light scatter with neutral density 1.0 filter. A total of 10,000 gated cells were analyzed for each histogram. Data were collected and processed as a 256 channel array using the EPICS V-MDADS system.

EXAMPLE 6

In Vitro Lymphoproliferation Assay

RPMI 1640 medium supplemented with L-glutamine (300 μg/ml), penicillin (100 U/ml), streptomycin (100 μg/ml, 2-mercaptoethanol ($5 \times 10^{-5}$M), Hepes (N-2-hydroxyethylpiperazine-N'-2-ethane-sulfonic acid, 1M), and 5% heat-inactivated FBS was used in the cell culture. T cell enriched lymphocytes were prepared from spleen cells using nylon wool (41° C. 1 hr) as described [Julius et al., Eur. J. Immunol. 3:645 (1973)]. Various concentrations of T lymphocytes were incubated with ConA (Pharmacia) at 41° C. in a humidified atmosphere of 6% $CO_2$ for 3 days. Twenty hours before harvesting, 1 uCi of $^3$H-thymidine ($^3$H-TdR; New England Nuclear, Boston, Mass.) was added. The cultures were harvested using a PHD cell harvester (Cambridge Technology, Inc., Cambridge, Mass.), and the amounts of radioactivity associated with cellular DNA were measured by liquid scintillation counting (Beckman Instruments, Irvine, Calif.). To determine the effects of MAb on T cell functions, cells binding to a specific MAb were killed prior to assay using complement (C)-mediated cell lysis as previously described [Lillehoj, supra].

EXAMPLE 7

Lymphoblastoid Tumor Cell Lines and Long-Term Cultured Spleen Cells

Three Marek's disease lymphoblastoid cell lines MDCC-CU15, CU36, and CU41 [Calnek et al., Infect. Immunity 34:483 (1981)] and LSCC-RP9 were used to screen the MAbs in an indirect fluorescent antibody assay. In addition, two long-term spleen cell cultures established from P-2a chickens in IL-2 containing medium with the morphology of large granular lymphocytes (LGL) [Schat et al., supra] were used to stain with CTLA MAbs.

EXAMPLE 8

MHC-Restricted CTL Assay

The procedure to assay MHC restricted cytotoxic T lymphocytes (CTL) against reticuloendotheliosis virus (REV) transformed target cells has been described [Weinstock and Schat, supra]. Briefly, effector cells were prepared by intraabdominal inoculation of 4-week-old P-2a chickens with 0.5 ml of cell-free, low virulence, tissue culture propagated REV containing $10^{4.2}$ $TCID_{50}$. Seven days post-inoculation, effector cells were removed from spleens and $15 \times 10^6$ cells were resuspended in LM-20 medium (RPMI 1640 containing 20% heat-inactivated fetal bovine serum). CTLA MAbs were evaluated by: (1) blocking of cytotoxicity in the CTL assay, and (2) antibody plus C mediated depletion of effector cells prior to CTL assay. Mouse MAb detecting chicken Ia antigens [Ewert et al., J. Immunol. 132:2524 (1984)] was used as a positive control. Mouse anti-rotavirus (Hernandez and Schat, unpublished observation) was used as a negative control since the determinants recognized by this MAb are not found on avian CTL or NK cells. Blocking of cytotoxicity was carried out by substituting into the 0.2 ml/well of LM-20, in which the effector and target cells were cocultured with 0.05 ml of MAb supernatant. Depletion of effector cells was carried out by treating $15 \times 10^6$ spleen cells with 0.1 ml of MAb or PBS (negative control), mouse anti-chicken Ia MAb, or an anti-rotavirus MAb for 15 min on ice. Cells were incubated for an additional 15 min on ice following addition of 0.1 ml of C-fixing rabbit anti-mouse immunoglobulin (Organon Teknika-Cappel, West Chester, Pa.). After washing in excess PBS, 0.3 ml of guinea pig C (GIBCO, Grand Island, N.Y.) was added, and cells were incubated for 45 min at 38° C. with occasional gentle agitation. Cells were washed in an excess of PBS, resuspended in LM-20, and used in the CTL assay. C-mediated cell lysis was evaluated by counting cells before and after treatment. The CTL assay was evaluated using a standard 4-hour cytotoxicity assay as previously described [Weinstock and Schat, supra]. Effector cells and $^{51}$Cr-labeled Cu-60 target cells were cocultured in triplicate for 4 hours at an effector to target (E:T) ration of 100:1 per well in 96-well round-bottom plates. The target cell line (RECC-CU60) was prepared from bone marrow cells from P-2a ($B^{19}B^{19}$) chickens. Target cells were labeled with $^{51}Cr$ as previously described [Weinstock and Schat, supra], resuspended in LM-20 medium, and used at 50,000 cells per well. Supernatant fluids and cell pellets lysed with 3% SDS were separately collected using the Skatron harvesting system (Skatron, Inc., Sterling, Va.). Radioactivity was quantitated by counting each sample for 10 min in a Beckman 4000 gamma counter (Beckman, Irvine, Calif.). The following calculations were made to evaluate the percent specific release (SR): (1) the percent release was calculated for each well by dividing counts per minute (CPM) of the supernatant fluid by the CPM of supernatant fluid plus cell pellet, and an average value of a triplicate set was obtained; (2) the mean percent release±standard deviation (SD) was calculated for each treatment group; and (3) the percent SR was obtained by subtracting the mean value for the control group from that for the experimental group. Levels of significance of percent specific release between groups were analyzed using the Student's test.

EXAMPLE 9

NK Cell Assay

The standard $^{51}Cr$-release assay with some modifications was used to assess natural killer cell activity [Chai and Lillehoj, supra]. Effector spleen lymphocytes were obtained from 5-week-old normal SC chickens. The chicken B cell line LSCC-RP9 ($B^2B^{15}$), derived from the avian lymphoid leukosis tumor transplant LSCT-RP6, was used as the target. Effector cells were cocultured with $^{51}Cr$-labeled target cells for 4 hrs at E:T cell ratio of 50:1. The percent specific release was calculated by the following formula: 100%×(test release−spontaneous release)/(total release−spontaneous release). Spontaneous release was calculated from the wells incubated with media, whereas total release was calculated from the wells incubated with 0.5% NP-40. In order to evaluate the blocking effect of CTLA MAbs on NK cell activity, P3X culture supernatant, mouse anti-chicken B-L MAb [Lillehoj et al., Poultry Sci., in press (1988)], MAb CTLA 3, 6, 4, or 9 were added into wells in which effector and target cells were cocultured at the beginning of the assay. To deplete effector cells mediating NK cell activity, spleen cells were pretreated with different MAb in the presence of rabbit C prior to assay.

EXAMPLE 10

Radiolabeling, Immunoprecipitation, and Gel Electrophoresis

Labeling of spleen cells with $^{125}I$ was performed using lactoperoxidase as described [Ewert et al., supra]. Labeled cells were immediately solubilized in lysing buffer, pH 7.5, containing 50 mM Tris, 0.15M NaCl, 1 mM EDTA, 0.01% $NaN_3$, 0.5% Nonidet P-40 (NP-40), 1 mM phenylmethyl-sulfonylfluoride (PMSF), and 1% aprotinin at 4° C. for 30 min. The detergent extracts were precleared by incubation with 250 $\mu l$ of 10% solution of protein A-agarose (Pharmacia) conjugated to rabbit anti-mouse serum for 30 min at 4° C. An aliquot of the precleared cell lysate was incubated with 1 $\mu l$ of MAb ascites for 1 hr at 4° C., Protein A-agarose conjugated with rabbit anti-mouse serum was then added to immunoprecipitate the antigen-antibody complexes. Immune complexes were washed 3 times with a buffer composed of 50 mM Tris, pH 8.0, 0.1M NaCl, 0.5% NP-40, 50 mM iodoacetamide, and 2 mM PMSF. The precipitated samples were then boiled for 5 min in 0.5M Tris, pH 6.8, containing 5% sodium dodecyl sulfate (SDS) and 0.1M DTT and subjected to electrophoresis on 10% acrylamide slab gels under reducing conditions according to the described method [Laemmli, Nature 277:680 (1970)]. After electrophoresis, the gels were fixed in acetic acid/methanol/water, dried onto filter paper, and subjected to autoradiography using a Kodax X-Omatic intensifer screen at −70° C. for 1 to 7 days.

I claim:

1. A hybridoma having the identifying characteristics of CTLA 1.

2. A hybridoma having the identifying characteristics of CTLA 3.

3. A monoclonal antibody produced by a hybridoma selected from the group consisting of CTLA 1 and CTLA 3.

4. A method of characterizing chicken T lymphocytes comprising contacting said T lymphocytes with a monoclonal antibody produced by a hybridoma selected from the group consisting of CTLA 1 and CTLA 3.

* * * * *